United States Patent
Louis

(10) Patent No.: US 9,394,248 B2
(45) Date of Patent: *Jul. 19, 2016

(54) PROCESS FOR THE MANUFACTURE OF DIHALODIPHENYLSULFONES

(75) Inventor: Chantal Louis, Alpharetta, GA (US)

(73) Assignee: SOLVAY SPECIALTY POLYMERS USA, LLC, Alpharetta, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/111,929

(22) PCT Filed: Apr. 12, 2012

(86) PCT No.: PCT/EP2012/056616
§ 371 (c)(1),
(2), (4) Date: Oct. 15, 2013

(87) PCT Pub. No.: WO2012/143281
PCT Pub. Date: Oct. 26, 2012

(65) Prior Publication Data
US 2014/0039222 A1 Feb. 6, 2014

Related U.S. Application Data

(60) Provisional application No. 61/476,419, filed on Apr. 18, 2011.

(51) Int. Cl.
*C07C 315/02* (2006.01)
*C07C 315/00* (2006.01)

(52) U.S. Cl.
CPC .................... *C07C 315/00* (2013.01)

(58) Field of Classification Search
USPC .......................... 568/28, 34, 35, 36
See application file for complete search history.

(56) References Cited

U.S. PATENT DOCUMENTS

| | | | |
|---|---|---|---|
| 3,415,887 A | 12/1968 | Keogh et al. | |
| 3,946,037 A | 3/1976 | Koebner | |
| 4,937,387 A | 6/1990 | Steiner | |
| 4,983,773 A | 1/1991 | Stumpp et al. | |
| 6,281,309 B1 * | 8/2001 | Babcock et al. | 526/201 |

FOREIGN PATENT DOCUMENTS

| | | |
|---|---|---|
| CN | 102304071 A2 | 1/2012 |
| WO | WO 2011067649 A2 | 6/2011 |
| WO | WO 2012/143279 A1 | 10/2012 |

OTHER PUBLICATIONS

Tyobeka T.E. et al., "Novel sulphonylating reagent : sulphuric acid-hexafluoroacetic anhydride", Journal of the Chemical Society, Chemical Communications, Jan. 1, 1980, p. 114-115—Chemical Society, Letchworth, GB.
Bourne E.J. et al., "155. Studies of trifluoroacetic acid. Part III. The use of trifluoroacetic anhydride in the synthesis of aromatic ketones and sulphones", J. Chem. Soc., 1951, p. 718-720—DOI: 10.1039/JR9510000718.
Tyobeka T.E. et al., "The interaction of hexafluoroacetic anhydride with methane sulfonic acid and with sulphuric acid", Tetrahedron, 1988, vol. 44, n°7, p. 1971-1978—Pergamon Press.
Hancock R.A. et al., "Regiospecificity and regioselectivity in syntheses of diaryl sulphones using the sulphuric acid-hexafluoroacetic anhydride reagent", Journal of Chemical Research (S), 1980, p. 270-271.
Alizadeh A. et al., "Rapid and mild sulfonylation of aromatic compounds with sulfonic acids via mixed anhydrides using Tf2O", Tetrahedron Letters, 2007, vol. 48, p. 6805-6808—Elsevier Ltd.
Third-Party Submission under 37 CFR 1.290 submitted Jan. 8, 2015 in U.S. Appl. No. 14/111,904 (24 pages).
Gilbert, et al.—Sulfonation and Sulfation with Sulfur Trioxide, Industrial and Engineering Chemistry, 1953, vol. 45, No. 9, p. 2065-2072 (8 pages).
U.S. Appl. No. 14/11,904, Chantal Louis et al., filed Oct. 15, 2013, WO 2012/143279.

* cited by examiner

*Primary Examiner* — Pancham Bakshi
(74) *Attorney, Agent, or Firm* — Jarrod N. Raphael; Dwight M. Benner, II

(57) ABSTRACT

A process for the preparation of dihalodiphenylsulfones_ such as 4,4'-dichlorodiphenyl sulfone or 4,4'-bis-(4-chlorophenylsulfonyl)biphenyl with high regioselectivity, at low temperature and in the absence of toxic reagents by reacting together at least one acid, at least one fluorinated anhydride and at least one halobenzene. The invented process is particularly suited for the manufacture of 4,4'-dichlorodiphenyl sulfone.

22 Claims, No Drawings

PROCESS FOR THE MANUFACTURE OF DIHALODIPHENYLSULFONES

RELATED APPLICATIONS

This application is a U.S. national stage entry under 35 U.S.C. §371 of International Application No. PCT/EP2012/056616, filed Apr. 12, 2012, which claims priority to U.S. Application No. 61/476,419 filed on Apr. 18, 2011, and the whole content of these applications is hereby incorporated herein by reference for all purposes.

FIELD OF THE INVENTION

The present invention relates to a new process for the manufacture of dihalodiphenylsulfones such as 4,4'-dichlorodiphenyl sulfone.

BACKGROUND OF THE INVENTION 4,4'-Dichlorodiphenyl sulfone, abbreviated as DCDPS, is an organic sulfone with the formula $(ClC_6H_4)_2SO_2$. It is most commonly used as a key monomer in the manufacture of sulfone polymers.

Other dihalodiphenylsulfones than 4,4'-dichlorodiphenyl sulfone and related derivatives are also of great industrial importance. One can mention inter alia 4,4'-bis-(4-chlorophenylsulfonyl)biphenyl or 4,4''-bis-(4-chlorophenylsulfonyl)terphenyl.

DCDPS can be prepared by various ways. It is generally prepared by a two-step Friedel-Crafts sulfonation and sulfonylation reaction.

DCDPS can be synthesized as described by U.S. Pat. No. 4,983,773 by treating chlorobenzene with sulfuric acid at a temperature of 200-250° C. The reaction can be done in the presence of boric acid or trifluoromethanesulfonic acid, which increases the DCDPS yield by reducing the formation of the 2,4' and 3,4' isomers. The reaction goes to completion in approximately 10 hours and produces a high yield of 4,4'-dichlorodiphenyl sulfone.

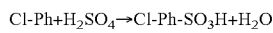

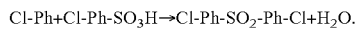

The use of high temperature leads to a decrease in selectivity (80-87% of the 4,4'-isomer) and also requires the use of expensive corrosion resistant material of construction.

The use of lower temperatures has also been described. It gives a higher regioselectivity but requires activated substrates.

U.S. Pat. No. 3,415,887 describes the synthesis of DCDPS starting from sulfur trioxide, diethylsulfate and chlorobenzene. The reaction is exothermic and external cooling must be employed to maintain the temperature to a level not greater than about 15° C. in order to limit the decomposition of intermediate products. The reaction is carried out at lower temperatures and leads to a higher regioselectivity. Dimethylsulfate may also be used in replacement of diethylsulfate. However, the use of diethylsulfate or dimethylsulfate has been firmly discouraged because of their great toxicity which causes significant issues associated with their use and transportation.

Tyobeka et al. describe in the *Journal of the Chemical Society, Chemical Communications* (1980), (3), 114-115, the use of a mixture of sulfuric acid and hexafluoroacetic anhydride as an efficient agent for the sulphonylation of aromatic compounds. In particular, they disclose the synthesis of DCDPS with 36% yield using monochlorobenzene, sulfuric acid and hexafluoroacetic anhydride in nitromethane. Nitromethane is carcinogen and explosive and its use is thus not recommended.

Thus, there remains an important need for an alternate route to manufacture dihalodiphenylsulfones and related derivatives with a high yield and high regioselectivity, at low temperature and in the absence of toxic or explosive reagents.

THE INVENTION

These needs are met by a process according to the present invention for the manufacture of a molecule (M) of the formula:

$$X-[Ar^1-SO_2-Ar^2]-[Ar^3]_n-[Ar^1-SO_2-Ar^2]_m-X \quad (M)$$

wherein n and m are independently 0, 1, 2, 3 or 4;
wherein X is an halogen selected from F, Cl, Br, I;
wherein $Ar^1$, $Ar^2$ are equal or different from each other and are aromatic moieties of the formula:

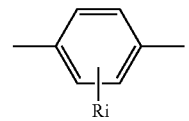

wherein $Ar^3$ is selected from the group consisting of:

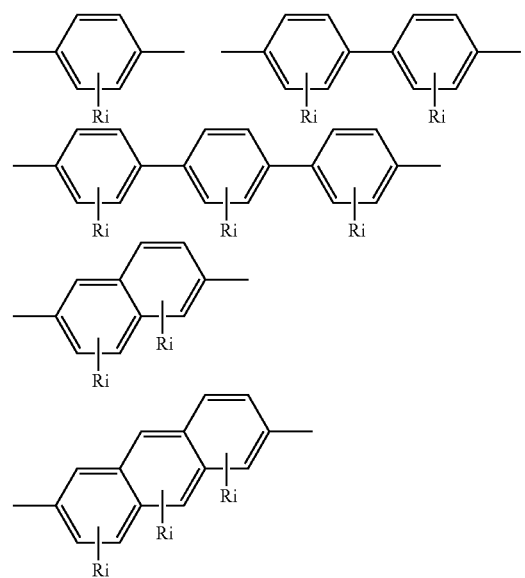

wherein each Ri is independently selected from the group consisting of: hydrogen, halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium;
by reacting together at least one acid selected from the group consisting of sulfuric acid, arene sulfonic acid or oleum, at least one fluorinated anhydride and at least one halobenzene;
and wherein the process is carried out in the absence of any solvent or in the presence of a solvent selected from the group consisting of: alkanes, chloroalkenes, chloroalkanes, di or tri-chlorobenzenes and carbon disulfide. The alkanes comprise preferably less than 8 C atoms, and the chloroalkanes comprise preferably less than 4 C atoms.

The process according to the present invention provides a lower cost alternate route to prepare the above mentioned molecules and in particular DCDPS at low temperature (below 140° C.) and high regioselectivity, without the use of expensive corrosion resistant material of construction.

DETAILED DESCRIPTION OF THE INVENTION

The present invention is directed to a process for the manufacture of a molecule (M) of the formula:

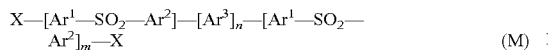
$$X—[Ar^1—SO_2—Ar^2]—[Ar^3]_n—[Ar^1—SO_2—Ar^2]_m—X \quad (M)$$

by reacting together at least one acid selected from the group consisting of sulfuric acid, arene sulfonic acid or oleum, at least one fluorinated anhydride and at least one halobenzene; and wherein the process is carried out in the absence of any solvent or in the presence of a solvent selected from the group consisting of: alkanes, chloroalkenes, chloroalkanes, halobenzenes and carbon disulfide.

When a solvent is used in the process according to the present invention, it is preferably selected from the group consisting of dichloromethane, 1,2-dichloroethane, chloroform, 1,1,2,2-tetrachloroethane, 1,2-dichlorobenzene, 1,2,4-trichlorobenzene, carbon disulfide, trichloroethylene, hexane, cyclohexane, heptane, and petroleum ether and more preferably selected from dichloromethane, 1,2-dichloroethane, 1,1,2,2-tetrachloroethane, 1,2-dichlorobenzene, 1,2,4-trichlorobenzene, trichloroethylene, hexane, cyclohexane, heptane, and petroleum ether Also, when a solvent is used in the process according to the present invention, it is preferably used in an amount of less than 15 wt %, more preferably less than 10 wt % and most preferably less than 5 wt % of the solvent, based on the total weight of the reagents. Most preferably, the reaction is carried out in the absence of any solvent.

When a halobenzene is used as a solvent, it may be the same or different from the halobenzene used as a reagent of the process according to the present invention.

In the molecule (M), n and m are preferably independently 0, 1 or 2, more preferably n and m are 0 or 1. Also, X is preferably selected from F and Cl. In addition, each Ri is preferably independently selected from the group consisting of hydrogens and halogens, more preferably all Ri's are hydrogens.

According to the present invention, the above mentioned "molecule (M)" may notably be one of the following molecules:

where X may be the same or different and are any halogen atoms chosen from chlorine, fluorine, bromine and iodine. The above structure may also be substituted by groups similar to the Ri described above.

In other words, the molecule (M) may be a dihalodiphenylsulfone such as 4,4'-dichlorodiphenyl sulfone, 4,4'-difluorodiphenyl sulfone, 4,4'-dibromodiphenyl sulfone and 4,4'-diiododiphenyl sulfone or mixed derivatives. Excellent results were obtained for the preparation of 4,4'-dichlorodiphenyl sulfone.

The molecule (M) may also be 4,4'-bis-(4-chlorophenylsulfonyl)biphenyl or 4,4"-bis-(4-chlorophenylsulfonyl)terphenyl.

In the process according to the present invention, the molecule (M) is prepared by reacting together at least one acid selected from the group consisting of sulfuric acid, arene sulfonic acid or oleum, at least one fluorinated anhydride and at least one halobenzene.

The fluorinated anhydride and the halobenzene used during the invented process are preferably dry, and feature preferably a purity level of at least 95%, more preferably at least 98% and most preferably at least 99%.

The "at least one fluorinated anhydride" used in the process according to the present invention may be selected from the group consisting of phosphoric, sulfonic and carboxylic anhydrides. It is preferably selected from the group consisting of sulfonic and carboxylic anhydrides. More preferably, it is selected from the anhydride of a perfluorinated alkane carboxylic acid (such as trifluoroacetic anhydride) or the anhydride of a perfluorinated alkane sulfonic acid (such as trifluoromethanesulfonic acid anhydride) or mixtures thereof. Still more preferably, the anhydride is a perfluorinated alkane carboxylic acid anhydride. Most preferably, it is trifluoroacetic anhydride (TFAA).

In the process according to the present invention, the "at least one acid" is selected from the group consisting of sulfuric acid, arene sulfonic acid or oleum is used. Preferably, the acid is sulfuric acid or 4-chlorobenzenesulfonic acid.

In a particular embodiment, at least two acids are used, the first acid being the one described above, the second one being a fluorinated acid. This last acid may be selected from perfluorinated alkane carboxylic acid such a trifluoroacetic acid or perfluorinated alkane sulfonic acid such as trifluoromethanesulfonic acid. It is preferably trifluoroacetic acid (TFA).

The term "halobenzene" is intended to denote any halogenated derivative of benzene. It may be mono-, di- or trihalogenated. The halobenzene is preferably a monohalobenzene where the halogen atom is chosen from chlorine, fluorine, bromine and iodine. More preferably, the halobenzene is monochlorobenzene (MCB).

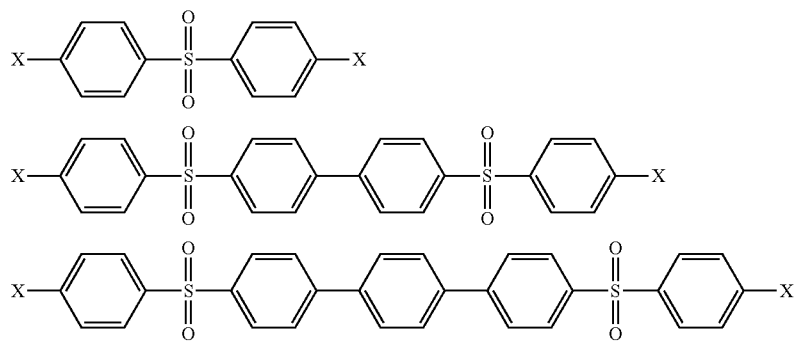

In a particular embodiment, the process according to the present invention is preferably carried out in the presence of a catalyst. If present, the catalyst is preferably used in an amount of from 0.2 to 50 g per mole of halobenzene, more preferably 1 to 10 g and most preferably 2 to 5 g. The catalyst optionally used in the present invention may be heterogeneous or homogeneous.

Non limitative examples of homogeneous catalysts are $ZnCl_2$ and $AlCl_3$, phosphoric acid, phosphonic acid, boric acid ($H_3BO_3$), boronic acid (an alkyl or aryl substituted boric acid), sulfonic, carboxylic acids or mixtures thereof. Boric acid is preferred.

Homogeneous catalysts may also be deposited on solid support such as clay, alumina, silica and zeolites.

In some particular embodiment, the catalyst is heterogeneous. Preferably, it is a solid acid catalyst. More preferably, the catalyst is selected from the group consisting of aluminosilicates, perfluoroalkanesulfonic acid resin and mixed oxide.

The solid acid catalyst is selected from the group of aluminosilicates, perfluoroalkanesulfonic acid resin (such as Nafion®-type) or mixed oxide (such as sulfated zirconia). Suitable aluminosilicates are crystalline aluminosilicates like acid-treated clays, for instance montmorillonite K10 and analogs, and zeolites, e.g. H-beta with $SiO/Al_2O_3$ ratio≤40. The H-beta zeolite and the montmorillonite K10 are the preferred catalyst. The H-beta zeolite is even more preferred. The catalyst shape is related to the process envisioned : pellets for fixed bed or powder for a slurry-type reactor. Both forms of catalyst are commercially available.

The process of the invention for the preparation of 4,4'-dichlorodiphenyl sulfone, starting from MCB and TFAA can be described according to the following reaction scheme (Scheme I):

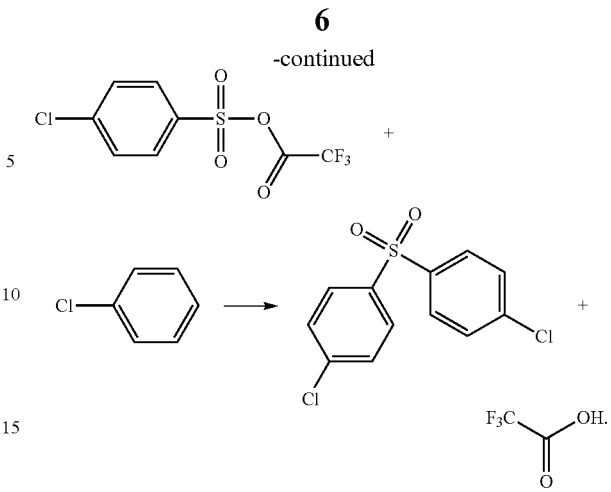

With the following overall equation: 2 MCB+2 TFAA+ $H_2SO_4 \rightarrow$ DCDPS+4 TFA.

Similarly, the process for the preparation of 4,4'-bis-(4-chlorophenylsulfonyl)biphenyl, can be described according to the following Scheme (II):

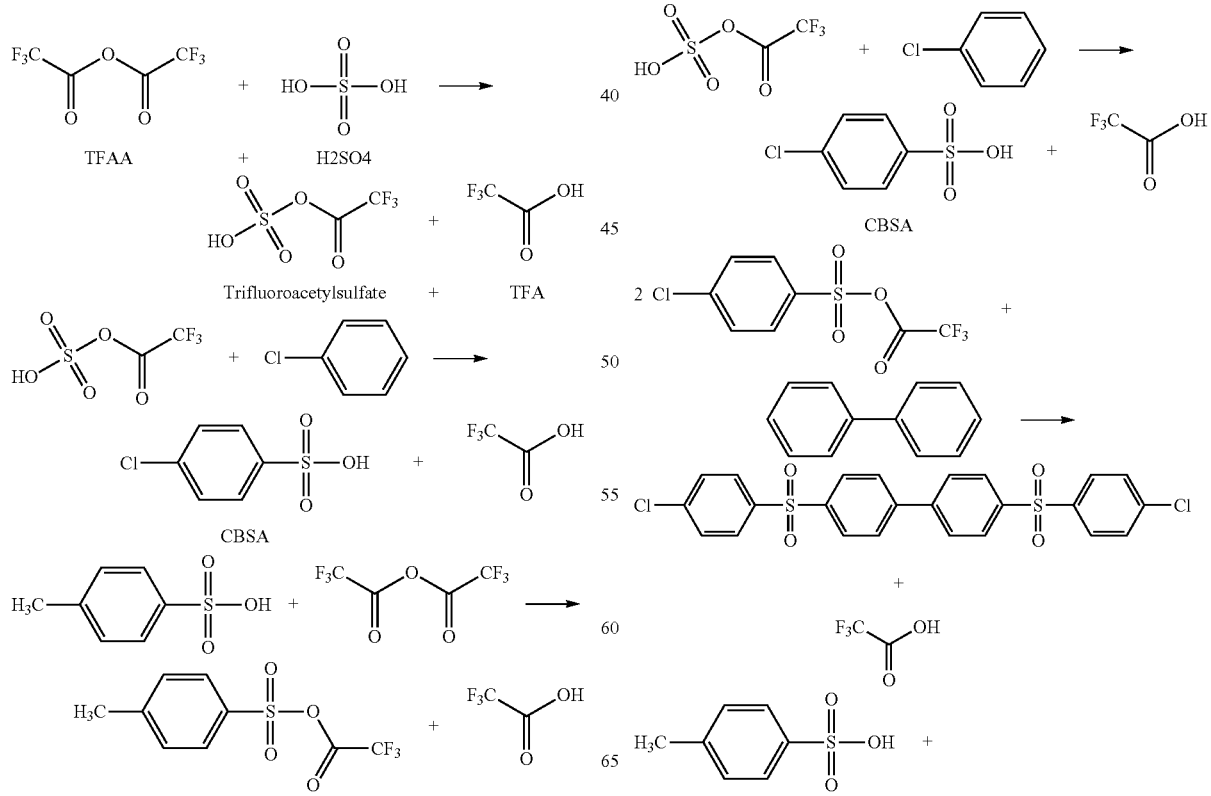

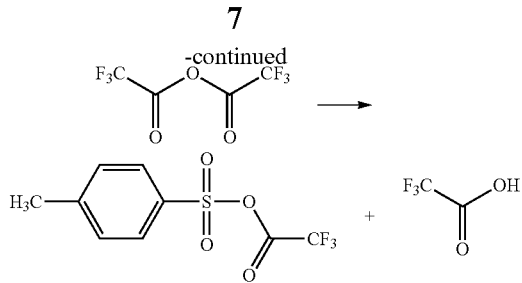

The process according to the present invention is preferably carried out at each step of the process at a temperature of below 140° C., more preferably of below 135° C., still more preferably of below 130° C. and most preferably of below 125° C. On the other hand, the process according to the present invention is preferably carried out at a temperature of above −40° C., more preferably of above −20° C., still more preferably of above −10° C. and most preferably of above 0° C.

The process according to the present invention is preferably carried out at a pressure of below 10 atm, more preferably of below 7 atm, still more preferably of below 5 atm and most preferably of below 2 atm. On the other hand, the process according to the present invention is preferably carried out at a temperature of above 0.5 atm, more preferably of above 0.6 atm, still more preferably of above 0.7 atm and most preferably of above 0.8 atm. Excellent results were obtained when the process according to the present invention was carried out at atmospheric pressure.

The process according to the present invention is preferably carried out under inert atmosphere, typically a nitrogen atmosphere, and essentially under anhydrous conditions.

In a particular embodiment, the process according to the present invention for the manufacture of a molecule (M) as above described comprises the following steps (a) to (e):
(a) At least one acid selected from the group consisting of sulfuric acid, arene sulfonic acid or oleum, at least one fluorinated anhydride, an optional fluorinated acid and an optional catalyst are added to a reaction medium at a temperature T1;
(b) The reaction medium is maintained at a temperature T2;
(c) At least one halobenzene is added to the reaction medium while the reaction medium is maintained at a temperature T2;
(d) The reaction medium is maintained at a temperature T3;
(e) The molecule (M) is isolated from the reaction medium.

In step (a), the temperature T1 is preferably of below 100° C., more preferably of below 80° C., still more preferably of below 60° C. and most preferably of below 40° C. On the other hand, the temperature T1 is preferably of above −40° C., more preferably of above −20° C., still more preferably of above 0° C. and most preferably of above 10° C. Excellent results were obtained when T1 was room temperature.

After step (a), the reaction medium is preferably maintained at a temperature T2. The temperature T2 is preferably of below 25° C., more preferably of below 20° C., still more preferably of below 15° C. and most preferably of below 12° C. On the other hand, the temperature T2 is preferably of above −40° C., more preferably of above −20° C., still more preferably of above −10° C. and most preferably of above −5° C. Excellent results were obtained when T2 was comprised between 0 and 10° C.

In step (c), the at least one halobenzene is preferably added very slowly, typically over a time of from 5 minutes to 10 hours, depending on the cooling capacity of the reaction medium. The reaction medium is preferably maintained at temperature T2 by external cooling means. Temperatures T2 may be the same or different in steps (b) and (c). Excellent results were also obtained when the process was carried out by adding a step (c*) where the reaction medium was maintained at a temperature T2', different from temperatures T2. The temperature T2' is chosen according to the preferred ranges described for the temperature T2 detailed above.

During step (d), the temperature is preferably maintained to at least one temperature T3. The temperature T3 is preferably of below 140° C., more preferably of below 135° C., still more preferably of below 130° C. and most preferably of below 125° C. On the other hand, the temperature T3 is preferably of above 10° C., more preferably of above 20° C., still more preferably of above 30° C. and most preferably of above 40° C. Good results were obtained when T3 was comprised between 30 and 125° C. Excellent results were also obtained when the process was carried out during step (d) at different temperatures T3.

In a preferred embodiment, and depending on the working pressure, the at least one fluorinated acid and the at least one fluorinated anhydride are partly distilled off the reaction medium during step (d). This allows increasing the reaction medium temperature T3 and the yield of the reaction.

The reaction medium is preferably homogeneous, until at least after step (c).

In step (e), the molecule (M) may be isolated from the reaction medium by precipitation, crystallization or extraction. Good results were obtained when the molecule (M) and in particular 4,4'-dichlorodiphenyl sulfone was isolated by precipitation in water or in methanol, by liquid-liquid extraction or by distillation under vacuum.

In another particular embodiment, the process according to the present invention for the manufacture of a molecule (M) as above described comprises the following steps (a') to (g'):
(a') At least one fluorinated anhydride, at least one acid selected from the group consisting of sulfuric acid, arene sulfonic acid or oleum, an optional fluorinated acid and an optional catalyst are added to a reaction medium at a temperature T1*
(b') The reaction medium is maintained at a temperature T2*;
(c') At least one halobenzene is added to the first reaction medium while the temperature is maintained at temperature T2*;
(d') The reaction medium is maintained at temperature T2*;
(e') Optionally, an additional amount of the at least one halobenzene or of an aromatic compound (A) is added to the reaction medium at a temperature T3*;
(f') The reaction medium is maintained at temperature T4*;
(g') The molecule (M) is isolated from the third reaction medium.

In step (a'), the temperature T1* is the same as temperature T1 as above described.

In steps (b') to (d'), the reaction medium is preferably maintained at a temperature T2*. The temperature T2* is preferably of below 60° C., more preferably of below 55° C., still more preferably of below 50° C. and most preferably of below 45° C. On the other hand, the temperature T2* is preferably of above −40° C., more preferably of above −20° C., still more preferably of above −10° C. and most preferably of above −5° C. Temperatures T2* may be the same or different in steps (b') to (d'). Excellent results were obtained when temperatures T2* were comprised between 0 and 45° C.

In steps (c') and (e'), the reaction medium is preferably maintained at temperature T2* or T3* by external cooling means.

In step (e'), the temperature T3* may be identical or different from T2* and is defined as defined above for T2*.

In step (f'), the second reaction medium is preferably maintained at a temperature T4*, defined as above for T3.

In step (e'), one may optionally add an additional amount of the at least one halobenzene or of an aromatic compound (A) to the third reaction medium, depending on the structure of the molecule (M) to be synthesized. Aromatic compound (A) is intended to denote any molecule comprising at least one aromatic group. Preferably, the aromatic compound (A) comprises at least two aromatic groups. Non-limiting examples of such aromatic compound (A) are: benzene, biphenyl, (ortho, meta or para) terphenyl, fluorene, naphthalene, anthracene, etc. For the synthesis of 4,4'-bis-(4-chlorophenylsulfonyl) biphenyl, biphenyl is used as the aromatic compound (A). The addition of aromatic compound (A) leads to the manufacture of a molecule (M) of the above described formula X—[$Ar^1$—$SO_2$—$Ar^2$]—[$Ar^3$]$_n$—[$Ar^1$—$SO_2$—$Ar^2$]$_m$—X where n≠0.

The reaction medium is preferably homogeneous, at least until after step (d).

The multistep process described above is particularly well adapted for the synthesis of asymmetric sulfones of the general formula X—$Ar^1$—$SO_2$—$Ar^2$—X wherein $Ar^1$ and $Ar^2$ are both aromatic groups but are different. In that case, $Ar^1$X, a halobenzene where X is as described above, is added in step (a'), while $Ar^2$X, is added at step (e').

In step (g'), the molecule (M) may be isolated from the reaction medium by precipitation, crystallization or extraction. Good results were obtained when the molecule (M) and in particular 4,4'-dichlorodiphenyl sulfone was isolated by precipitation in water or in methanol, by liquid-liquid extraction or by distillation under vacuum.

At the end of the reaction, the fluorinated acid obtained from the reaction of the fluorinated anhydride can be recycled. Recycling may be achieved by well known methods.

The process according to the present invention is preferably carried out using specific molar ratios of the different reagents.

Preferably, the molar ratio of the fluorinated anhydride to the at least one halobenzene is from 0.20 to 12, more preferably from 0.60 to 2.5. Excellent results were obtained when the ratio was from 0.80 to 2.

Preferably, the molar ratio of the at least one fluorinated acid to the at least one halobenzene is from 0 to 6, more preferably from 0 to 3, most preferably from 0.10 to 2. Excellent results were obtained when the ratio was from 0.20 to 1.

Preferably, the molar ratio of the at least one acid selected from the group consisting of sulfuric acid, arene sulfonic acid or oleum to the at least one halobenzene is from 0.10 to 10, more preferably from 0.20 to 5, most preferably from 0.3 to 3. Excellent results were obtained when the ratio was from 0.4 to 2.

The process according to the present invention is preferably carried out in one pot. The term "one pot" when referred to a reaction is generally intended to denote any reaction where a reactant is subjected to successive chemical reactions in just one reactor, thereby avoiding a lengthy separation process and purification of the intermediate chemical compounds.

Depending on the quantity and the reactivity of the reagents, the conditions chosen for carrying out the process according to the invention, the reaction can take place in a few minutes or in several hours.

Still another aspect of the present invention is directed to the use of at least one fluorinated anhydride and at least one acid selected from the group consisting of sulfuric acid, arene sulfonic acid or oleum in the presence a halobenzene for the synthesis of a molecule (M), preferably a dihalodiphenylsulfone.

Should the disclosure of any patents, patent applications, and publications which are incorporated herein by reference conflict with the description of the present application to the extent that it may render a term unclear, the present description shall take precedence.

EXAMPLES

Examples and comparative examples 1 to 15 below relate to the synthesis of 4,4'-dichlorodiphenyl sulfone.

Examples 1 to 7 of Table 1 were carried out according to the present invention at a temperature of up to 100° C. and feature surprisingly a very high level of regioselectivity and excellent yields when reagents and conditions are tuned (see table 1).

Examples C8 to C11 were carried out in the presence of nitromethane, as taught by Tyobeka et al., and lead to low yields. The presence of nitromethane in an amount of only 5% resulted in a drop of the yield of almost 50% (see example 1 and C8), the yield reached only 14% in the presence of 52% nitromethane.

Examples 12 and 13 of Table 2 were carried out according to the present invention at a temperature of up to 60° C. and feature surprisingly a very high level of regioselectivity and good yields.

Examples 14 and C15 of Table 3 were carried out at a temperature of up to 120° C. Example 14 features moderate selectivity and yields while example C15 using a non fluorinated anhydride under the same conditions leads to dramatically low yield.

Examples and comparative examples 16 to 17 of Table 4 below relate to the synthesis of 4,4'-bis-(4-chlorophenylsulfonyl)biphenyl.

The following reagents were used to carry out the examples:
Concentrated $H_2SO_4$: J. T. Baker, analyzed, 95.9 wt %.
Monochlorobenzene: MCB, PPG, 99%.
Trifluoromethanesulfonic acid (TfOH, Aldrich, 98%).
Trifluoroacetic acid: TFA, Aldrich, 99%.
Trifluoroacetic anhydride: TFAA, Aldrich, 99%.
Acetic anhydride: Aldrich, 99.5%.
Boric acid: Aldrich, ACS reagent, ≥99.5%.
Nitromethane: Aldrich, for HPLC, ≥96%.
Aromatic compound: Biphenyl (Aldrich reagent Plus, 99.5%).
Solid acid catalysts:
  Nanocomposite of amorphous silica and perfluorinated sulfonic acid resin Nafion®: Nafion®SAC 13, Aldrich-2-3 mm extrudates, not dried;
  Montmorillonite K10, Acros—dried at 120° C./0.3 atm for 12 hours before use;
  Zeolite H-beta, ZEOCHEM®: Zeocat® PB-H 25 powder, $SiO_2/Al_2O_3$=30.3 mol/mol, 524 $m^2$/g BET surface area, 8-10 μm average particle size—dried at 500° C. under air for 12 hours before use;
  Zeolite H-beta, ZEOCHEM®: Zeocat® PB-H 25, pellets, 2.0-3.0 mm, dried at 500° C. under air for 12 hours before use;
  Zeolite H-ZSM5, ZEOCHEM®: Zeocat®PZ-2/25-H, powder, $SiO_2/Al_2O_3$=25 mol/mol, 450 $m^2$/g BET surface area, 8-10 μm average particle size—dried at 500° C. under air for 12 hours before use;
  Sulfated zirconia, MEL Chemicals, XZ01249101, 7 wt % $SO_3$, 400 $m^2$/g BET surface area, 5 μm average particle size—dried at 500° C. under air for 12 hours before use;

Zeolite NH$_4$-β: Tosoh, HSZ-930NHA, powder, SiO$_2$/Al$_2$O$_3$=27 mol/mol, 630 m$^2$/g BET surface area, 3-6 μm average particle size, dried at 500° C. under air for 12 hours before use.

Example 1

With TFAA, in the Absence of a Solid Catalyst

In a dry 3-neck 250-mL round bottom flask, fitted with a thermocouple, a distillation receiver allowing returning the vapors to the mixture (Barrett trap)+reflux condenser+silicone oil bubbler, and containing a PTFE-coated stir bar, were introduced successively:
1. 10.23 g of concentrated H$_2$SO$_4$
2. 34.66 g of TFA
3. 125.99 g of TFAA.

The 3$^{rd}$ neck of the flask was then sealed with a stopper. The mixture was cooled down to 10° C. with an ice bath and 54.32 g of MCB were added. The temperature of the reaction medium was maintained to 10° C. with an ice bath during the addition. After the end of the addition, the ice bath was replaced with a heating mantle and the temperature was increased to 40° C. The reaction medium was held at 40° C. for 1 hour, then heated to 53° C. The reaction medium was held at 53° C., under reflux conditions, for 3 hours. The distillation receiver was then placed in the collecting position (liquid not refluxed back to the mixture) and the reaction medium temperature was increased to 100° C. At 100° C., 146.89 g of distillate had been collected. The empty distillation receiver was thus returned to total reflux conditions and the reaction medium was held at 100° C. for 3 hours. At the end of the reaction, the mixture was poured on 1,000 mL of deionized water. The precipitate formed was isolated by filtration, rinsed with more deionized water (1,000 mL) and dried at 60° C./0.3 atm for 20 hours. The dried solid (1.73 g) was analyzed by GC and shown to be 4,4'-dichlorodiphenyl sulfone (95.8% 4,4'-isomer), 59% yield.

Example 2

With Nafion® SAC13

The same procedure as for example 1 was followed except that a solid acid Nafion® catalyst was introduced into the flask with H$_2$SO$_4$:
Reagents:
1. 10.15 g of concentrated H$_2$SO$_4$
2. 2.39 g Nafion® SAC13 (2-3 mm extrudates, not dried)
3. 34.69 g of TFA
4. 125.11 g of TFAA.

58.35 g of MCB were added at 10° C. 144.91 g of distillate were collected at 100° C. At the end of the reaction, 24.11 g of 4,4'-dichlorodiphenyl sulfone were isolated after removal of the catalyst by filtration on Buchner funnel and precipitation of 4,4'-dichlorodiphenyl sulfone in the filtrate with water (95.1% 4,4'-isomer), 84% yield.

Example 3

With Montmorillonite K10

The same procedure as for example 1 was followed except that a solid acid montmorillonite catalyst was introduced into the flask with H$_2$SO$_4$:
Reagents:
1. 10.25 g of concentrated H$_2$SO$_4$
2. 2.51 g montmorillonite
3. 34.31 g of TFA
4. 127.57 g of TFAA.

57.32 g of MCB were added at 10° C. 149.89 g of distillate was collected at 100° C. At the end of the reaction, 23.18 g of 4,4'-dichlorodiphenyl sulfone were isolated after removal of the catalyst by filtration under pressure and precipitation of 4,4'-dichlorodiphenyl sulfone in the filtrate with water (96.1% 4,4'-isomer), 80% yield.

Example 4

With Zeolite H-β

The same procedure as for example 1 was followed except that a solid acid zeolite H-β catalyst was introduced into the flask with H$_2$SO$_4$:
Reagents:
1. 10.21 g of concentrated H$_2$SO$_4$
2. 2.51 g zeolite H-β
3. 22.80 g of TFA
4. 84.64 g of TFAA.

56.30 g of MCB were added at 10° C. 88.38 g of distillate were collected at 100° C. At the end of the reaction, 28.72 g of 4,4'-dichlorodiphenyl sulfone were isolated after removal of the catalyst by filtration under pressure and precipitation of 4,4'-dichlorodiphenyl sulfone in the filtrate with water (96.9% 4,4'-isomer), 100% yield.

Example 5

With Zeolite H-ZSM5

The same procedure as for example 1 was followed except that a solid acid zeolite H-ZSM catalyst was introduced into the flask with H$_2$SO$_4$:
Reagents:
1. 10.23 g of concentrated H$_2$SO$_4$
2. 2.52 g zeolite H-ZSM5
3. 34.20 g of TFA
4. 126.01 g of TFAA.

56.28 g of MCB were added at 10° C. 148.87 g of distillate were collected at 100° C. At the end of the reaction, 12.18 g of 4,4'-dichlorodiphenyl sulfone were isolated after removal of the catalyst by filtration under pressure and precipitation of 4,4'-dichlorodiphenyl sulfone in the filtrate with water (94.6% 4,4'-isomer), 42% yield.

Example 6

With Sulfated Zirconia

The same procedure as for example 1 was followed except that a solid acid sulfated zirconia catalyst was introduced into the flask with H$_2$SO$_4$:
Reagents:
1. 10.23 g of concentrated H$_2$SO$_4$
2. 2.46 g sulfated zirconia
3. 34.13 g of TFA
4. 126.48 g of TFAA.

58.76 g of MCB were added at 10° C. 144.36 g of distillate were collected at 100° C. At the end of the reaction, 10.88 g of 4,4'-dichlorodiphenyl sulfone were isolated after removal of the catalyst by filtration under pressure and precipitation of 4,4'-dichlorodiphenyl sulfone in the filtrate with water (92.8% 4,4'-isomer), 37% yield.

Example 7

With Boric Acid

The same procedure as for example 1 was followed except that boric acid was introduced into the flask with $H_2SO_4$ and TFAA:
1. 2.64 g of boric acid
2. 20.40 g of concentrated $H_2SO_4$
3. 105.21 g of TFAA.

Then, 56.30 g of MCB were added at 10° C. and the temperature profile used afterwards was 40/60/100° C. instead of 40/53/100. 78.80 g of distillate were collected before reaching 100° C. The dried solid (53.90 g) was analyzed by GC and shown to be 4,4'-dichlorodiphenyl sulfone (95.8% 4,4'-isomer), 94% yield.

Comparative Example 8

With 5 wt % Nitromethane in the Initial Reaction Medium

The same procedure as for example 7 was followed except that nitromethane was introduced into the flask together with $H_2SO_4$, TFA and TFAA:
1. 9.88 g nitromethane
2. 17.85 g of concentrated $H_2SO_4$
3. 10.02 g of TFA
4. 110.87 g of TFAA.

Then 49.27 g of MCB were added at 10° C. 106.65 g of distillate were collected before reaching 100° C. The dried solid (14.70 g) was analyzed by GC and shown to be 4,4'-dichlorodiphenyl sulfone (94.5% 4,4'-isomer), 29% yield Comparative Example 9

With 10 wt % Nitromethane in the Initial Reaction Medium

The same procedure as for example 7 was followed except that nitromethane was introduced into the flask together with $H_2SO_4$, TFA and TFAA:
1. 20.83 g nitromethane
2. 17.82 g of concentrated $H_2SO_4$
3. 9.97 g of TFA
4. 110.41 g of TFAA.

Then 49.30 g of MCB were added at 10° C. 119.43 g of distillate were collected before reaching 100° C. The dried solid (13.67 g) was analyzed by GC and shown to be 4,4'-dichlorodiphenyl sulfone (95.0% 4,4'-isomer), 29% yield.

Comparative Example 10

With 15 wt % Nitromethane in the Initial Reaction Medium

The same procedure as for example 7 was followed except that nitromethane was introduced into the flask together with $H_2SO_4$, TFA and TFAA:
1. 33.06 g nitromethane
2. 17.83 g of concentrated $H_2SO_4$
3. 10.03 g of TFA
4. 110.61 g of TFAA.

Then 49.25 g of MCB were added at 10° C. 92.08 g of distillate were collected before reaching 100° C. The dried solid (14.30 g) was analyzed by GC and shown to be 4,4'-dichlorodiphenyl sulfone (95.6% 4,4'-isomer), 28% yield.

Comparative Example 11

With 52 wt % Nitromethane in the Initial Reaction Medium

The same procedure as for example 7 was followed except that nitromethane was introduced into the flask together with $H_2SO_4$, TFA and TFAA:
1. 115.99 g nitromethane
2. 10.19 g of concentrated $H_2SO_4$
3. 5.72 g of TFA
4. 63.62 g of TFAA.

Then 28.16 g of MCB were added at 10° C. 24.55 g of distillate were collected before reaching 100° C. The dried solid (3.90 g) was analyzed by GC and shown to be 4,4'-dichlorodiphenyl sulfone (95.7% 4,4'-isomer), 14% yield.

Example 12

With zeolite H-β, at Lower Temperature

In a dry 3-neck 250-mL round bottom flask, fitted with a thermocouple, a distillation receiver allowing returning the vapors to the mixture (Barrett trap)+reflux condenser+silicone oil bubbler, and containing a PTFE-coated stir bar, were introduced successively:
1. 14.32 g of concentrated $H_2SO_4$
2. 2.52 g zeolite H-β
3. 24.05 g of TFA
4. 88.59 g of TFAA.

The 3$^{rd}$ neck of the flask was then sealed with a stopper. The mixture was cooled down to 10° C. with an ice bath and 78.84 g of MCB were added. The temperature of the reaction medium was maintained to 10° C. with an ice bath during the addition. After the end of the addition, the ice bath was replaced with a heating mantle and the temperature was increased to 60° C. under total reflux conditions. The reaction medium was held at 60° C. for 6 hours. At the end of the reaction, the catalyst was removed by filtration under pressure and the filtrate was poured on 1,500 mL of deionized water. The precipitate formed was isolated by filtration, rinsed with more deionized water (1,500 mL) and dried at 60° C./0.3 atm for 20 hours. The dried solid (22.73 g) was analyzed by GC and shown to be 4,4'-dichlorodiphenyl sulfone (96.4% 4,4'-isomer), 57% yield.

Example 13

With Zeolite $NH_4$-β, at Lower Temperature

The same procedure as for example 12 was followed except that the solid acid catalyst was a zeolite $NH_4$-β0 was introduced into the flask with $H_2SO_4$:
Reagents:
1. 14.21 g of concentrated $H_2SO_4$
2. 2.53 g zeolite $NH_4$-β
3. 23.92 g of TFA
4. 88.45 g of TFAA.

78.79 g of MCB were added at 10° C. At the end of the reaction, 30.01 g of 4,4'-dichlorodiphenyl sulfone were isolated after removal of the catalyst by filtration under pressure and precipitation of 4,4'-dichlorodiphenyl sulfone in the filtrate with water (96.9% 4,4'-isomer), 74% yield.

Example 14

Starting from Chlorobenzenesulfonic Acid in the Absence of a Solid Acid Catalyst A mixture of 4-chlorobenzenesulfonic acid was produced by the reaction of MCB with sulfur trioxide. The mixture contained 70 wt % chlorobenzenesulfonic acid (96.5% 4-isomer), 21 wt % dichlorodiphenyl sulfone (94.2 4,4'-isomer), 7 wt % $H_2SO_4$ and 2 wt % MCB.

In a dry 3-neck 250-mL round bottom flask, fitted with a thermocouple, a distillation receiver allowing returning the vapors to the mixture (Barrett trap)+reflux condenser+silicone oil bubbler, and containing a PTFE-coated stir bar, were introduced successively:

1. 55.10 g of the chlorobenzenesulfonic acid mixture (=38.57 g acid, 11.57 g sulfone)
2. 34.22 g of TFA
3. 63.14 g of TFAA.

The 3$^{rd}$ neck of the flask was then sealed with a stopper. The mixture was heated to 40° C. for 30 minutes, then 33.81 g of MCB were added. The temperature of the reaction medium was increased to 53° C. under total reflux conditions. The reaction medium was held at 53° C. for 3 hours. The distillation receiver was then placed in the collecting position (liquid not refluxed back to the recation medium) and the reaction medium temperature was increased to 100° C. At 100° C., 75.83 g of distillate had been collected. At the end of the reaction, the reaction medium was poured on 1,000 mL of deionized water. The precipitate formed was isolated by filtration, rinsed with more deionized water (1,000 mL) and dried at 60° C./0.3 atm for 20 hours. The dried solid (55.330 g) was analyzed by GC and shown to be 4,4'-dichlorodiphenyl sulfone (93.8% 4,4'-isomer), 62% yield. Taking into account the isomeric purity of the dichlorodiphenyl sulfone (94.2%) present in initial 4-chlorobenzenesulfonic acid, the regioselectivity of the sulfonylation step with TFAA is 93.7%.

Comparative Example 15

Starting from Chlorobenzenesulfonic Acid with Acetic Anhydride Instead of TFAA

A mixture of 4-chlorobenzenesulfonic acid was produced by the reaction of MCB with sulfur trioxide. The mixture contained 70 wt % chlorobenzenesulfonic acid (96.5% 4-isomer), 21 wt % dichlorodiphenyl sulfone (94.2% 4,4'-isomer), 7 wt % $H_2SO_4$ and 2 wt % MCB.

In a dry 3-neck 250-mL round bottom flask, fitted with a thermocouple, a distillation receiver allowing returning the vapors to the mixture (Barrett trap)+reflux condenser+silicone oil bubbler, and containing a PTFE-coated stir bar, were introduced successively:

1. 40.98 g of the chlorobenzenesulfonic acid mixture (=28.69 g acid, 8.61 g sulfone)
2. 18.15 g of acetic anhydride.

The 3$^{rd}$ neck of the flask was then sealed with a stopper. The mixture was heated to 120° C. under total reflux conditions and held at 120° C. for 20 minutes. Then, at 120° C., 69.74 g of MCB were added. The temperature of the reaction medium was decreased to 100° C. under total reflux conditions. The reaction medium was held at 100° C. for 3 hours. At the end of the reaction, the reaction medium was poured on 1,000 mL of deionized water. The precipitate formed was isolated by filtration, rinsed with more deionized water (1,000 mL) and dried at 60° C./0.3 atm for 20 hours. The dried solid (8.95 g) was analyzed by GC and shown to be 4,4'-dichlorodiphenyl sulfone (94.6% 4,4'-isomer), 2% yield.

Example 16

Preparation of 4,4'-bis-(4-chlorophenylsulfonyl)biphenyl in the Presence of a Solid Acid Catalyst In a dry 3-neck 250-mL round bottom flask, fitted with a thermocouple, a distillation receiver allowing returning the vapors to the mixture (Barrett trap)+reflux condenser+silicone oil bubbler, and containing a PTFE-coated stir bar, were introduced successively:

1. 3.92 g Nafion® SAC13
2. 20.39 g of concentrated $H_2SO_4$
3. 107.77 g of TFAA.

The 3$^{rd}$ neck of the flask was then sealed with a stopper. The mixture was cooled down to 10° C. with an ice bath and 22.520 g of MCB were added. The temperature of the reaction medium was maintained to 10° C. with an ice bath during the addition and then held at 10° C. for one hour. The ice bath was then replaced with a heating mantle and the temperature was increased to 40° C. The reaction medium was held at 40° C. for 1 hour. 12.34 g biphenyl was then added to the reaction via the central neck. The reaction medium turned pink and was then heated to 53° C. and held at 53° C. for 3 hours. The distillation receiver was then placed in the collecting position (liquid not refluxed back to the reaction medium) and the reaction medium temperature was increased to 100° C. At 100° C., 78.78 g of distillate had been collected. The empty distillation receiver was thus returned to total reflux conditions and the purple reaction medium was held at 100° C. for 3 hours and 30 minutes. A solid formed during that period. At the end of the reaction, the mixture was analyzed by HPLC and shown to contain 19.0 wt % 4,4'-bis-(4-chlorophenylsulfonyl)biphenyl by comparison with a commercially available standard (Aldrich, 98%), 40% yield.

Example 17

Preparation of 4,4'-bis-(4-chlorophenylsulfonyl)biphenyl in the Presence of Boric Acid In a dry 3-neck 250-mL round bottom flask, fitted with a thermocouple, a distillation receiver allowing returning the vapors to the mixture (Barrett trap)+reflux condenser+silicone oil bubbler, and a mechanical stirrer, were introduced successively:

1. 2.63 g of boric acid
2. 20.41 g of concentrated $H_2SO_4$
3. 99.70 g of TFA
4. 105.11 g of TFAA.

The 3$^{rd}$ neck of the flask was then sealed with a stopper. The mixture was cooled down to 10° C. with an ice bath and 22.52 g of MCB were added. The temperature of the reaction medium was maintained to 10° C. with an ice bath during the addition and then held at 10° C. for one hour. The ice bath was then replaced with a heating mantle and the temperature was increased to 40° C. The reaction medium was held at 40° C. for 1 hour. 12.34 g biphenyl was then added to the reaction via the central neck. The reaction medium turned pink and was then heated to 50° C. and held at 50° C. for 3 hours. The distillation receiver was then placed in the collecting position (liquid not refluxed back to the mixture) and the reaction medium temperature was increased to 75° C. At 75° C., 138.92 g of distillate had been collected. The empty distillation receiver was thus returned to total reflux conditions and the purple reaction medium was held at 75° C. for 3 hours. A solid formed during that period. At the end of the reaction, the mixture was analyzed by HPLC and shown to contain 10.1 wt % 4,4'-bis-(4-chlorophenylsulfonyl)biphenyl by comparison with a commercially available standard (Aldrich, 98%), 30% yield.

TABLE 1 synthesis of DCDPS starting from H₂SO₄, one pot sulfonation and sulfonylation at temperature up to 100° C.

| Example | Anhydride | Additional fluorinated acid | Catalyst | Solvent | DCDPS yield (mol %) | 4,4'-DCDPS selectivity (mol %) |
|---|---|---|---|---|---|---|
| 1 | TFAA | TFA | None | None | 59 | 95.2 |
| 2 | TFAA | TFA | Nafion ® SAC13 | None | 84 | 95.1 |
| 3 | TFAA | TFA | Montmorillonite K10 | None | 80 | 96.1 |
| 4 | TFAA | TFA | H-β Zeochem ® | None | 100 | 96.9 |
| 5 | TFAA | TFA | H-ZSM5 Zeochem ® | None | 42 | 94.6 |
| 6 | TFAA | TFA | ZrO₂/SO₃ | None | 37 | 92.8 |
| 7 | TFAA | None | Boric acid | None | 94 | 95.8 |
| C8 | TFAA | TFA | None | 5% nitromethane | 29 | 94.5 |
| C9 | TFAA | TFA | None | 10% nitromethane | 29 | 95.0 |
| C10 | TFAA | TFA | None | 15% nitromethane | 28 | 95.6 |
| C11 | TFAA | TFA | None | 52% nitromethane | 14 | 95.7 |

TABLE 2 synthesis of DCDPS starting from H₂SO₄, one pot sulfonation and sulfonylation at temperature up to 60° C.

| Example | Anhydride | Additional fluorinated acid | Catalyst | Solvent | DCDPS yield (mol %) | 4,4'-DCDPS selectivity (mol %) |
|---|---|---|---|---|---|---|
| 12 | TFAA | TFA | H-β Zeochem ® | None | 57 | 96.4 |
| 13 | TFAA | TFA | NH4-β Tosoh | None | 74 | 96.9 |

TABLE 3 synthesis of DCDPS starting from chlorobenzenesulfonic acid, sulfonylation only at temperature up to 120° C.

| Example | Anhydride | Additional fluorinated acid | Catalyst | Solvent | DCDPS yield (mol %) | 4,4'-DCDPS selectivity (mol %) |
|---|---|---|---|---|---|---|
| 14 | TFAA | TFA | None | None | 62 | 93.7 |
| C15 | Acetic anhydride | None | None | None | 2 | 94.6 |

TABLE 4 synthesis of 4,4'-bis-(4-chlorophenylsulfonyl)biphenyl starting from chlorobenzenesulfonic acid, sulfonylation only at temperature up to 120° C.

| Example | Anhydride | Additional fluorinated acid | Catalyst | Solvent | yield (mol %) |
|---|---|---|---|---|---|
| 16 | TFAA | None | Nafion ® SAC13 | None | 40 |
| 17 | TFAA | TFA | Boric acid | None | 30 |

The invention claimed is:

1. A process for making molecule of the formula (M):

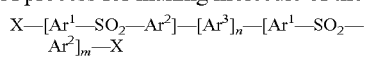

wherein:
n and m are independently 0, 1, 2, 3 or 4;
X is a halogen selected from F, Cl, Br, I;
$Ar^1$, $Ar^2$ are equal or different from each other and are aromatic moieties of the formula:

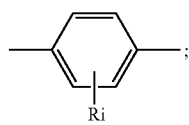

$Ar^3$ is selected from the group consisting of:

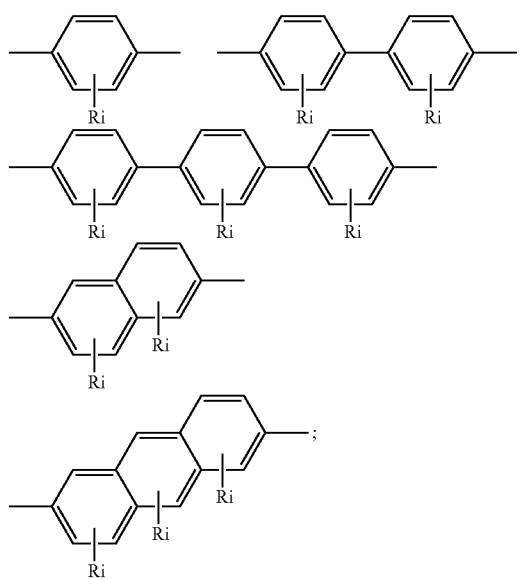

and each Ri is independently selected from the group consisting of: hydrogen, halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium;

by reacting together at least one acid selected from the group consisting of sulfuric acid, arene sulfonic acid or oleum, at least one fluorinated anhydride; at least one halobenzene; at least one fluorinated acid and, optionally, an aromatic compound; wherein the process is carried out in the presence of a catalyst selected from the group consisting of boric acid, boronic acid, aluminosilicates, perfluoroalkanasulfonic acid resins, mixed oxides, and mixtures thereof, and in the absence of any solvent or in the presence of a solvent selected from the group consisting of: alkanes, chloroalkenes, chloroalkanes, halobenzenes and carbon disulfide.

2. The process according to claim 1, wherein the fluorinated anhydride is selected from the group consisting of phosphoric, sulfonic and carboxylic anhydrides.

3. The process according to claim 2, wherein the fluorinated anhydride is a carboxylic anhydride.

4. The process according to claim 3, wherein the carboxylic anhydride is trifluoromethanesulfonic acid anhydride or trifluoroacetic anhydride.

5. The process according to claim 1, wherein the molecule of the formula (M) is a dichlorodiphenyl sulfone.

6. The process according to claim 1, wherein the process is carried out in the absence of any solvent.

7. The process according to claim 1, wherein the solvent is selected from the group consisting of dichloromethane, 1,2-dichloroethane, chloroform, 1,1,2,2-tetrachloroethane, 1,2-dichlorobenzene, 1,2,4-trichlorobenzene, carbon disulfide, trichloroethylene, hexane, cyclohexane, heptane, and petroleum ether.

8. The process according to claim 1, wherein the process comprises the following steps:
(a) the at least one acid selected from the group consisting of sulfuric acid, arene sulfonic acid or oleum, the at least one fluorinated anhydride, an optional fluorinated acid, and the catalyst are added to a reaction medium at a temperature T1;
(b) the reaction medium is maintained at a temperature T2;
(c) the at least one halobenzene is added to the reaction medium while the reaction medium is maintained at a temperature T2;
(d) the reaction medium is maintained at a temperature T3;
(e) the molecule of the formula (M) is isolated from the reaction medium.

9. The process according to claim 1, wherein it is done in one pot.

10. The process according to claim 1, wherein the process is carried out at a temperature that does not exceed 140° C.

11. The process of claim 1, wherein the aromatic compound is selected from benzene, biphenyl, terphenyl, fluorene, naphthalene, and anthracene.

12. The process of claim 1, wherein the molecule of formula (M) is made by reacting together the at least one acid, the at least one fluorinated anhydride; the at least one halobenzene, and wherein n=0, and m=0.

13. The process of claim 12, wherein the at least one acid is sulfuric acid, the at least one fluorinated anhydride is trifluoroacetic anhydride, the at least one halobenzene is monochlorobenzene, and the molecule of formula (M) is 4,4'-dichlorodiphenyl sulfone.

14. The process of claim 1, wherein the molecule of formula (M) is made by reacting together the at least one acid, the at least one fluorinated anhydride; the at least one halobenzene, and an aromatic compound selected from benzene, biphenyl, terphenyl, fluorene, naphthalene, and anthracene, and wherein n≠0.

15. The process of claim 14, wherein the at least one acid is sulfuric acid, the at least one fluorinated anhydride is trifluoroacetic anhydride, the at least one halobenzene is monochlorobenzene, the aromatic compound is biphenyl, and the molecule of formula (M) is 4,4"-bis-(4-chlorophenylsulfonyl)biphenyl.

16. A process for making a molecule of the formula (M):

$$X-[Ar^1-SO_2-Ar^2]-[Ar^3]_n-[Ar^1-SO_2-Ar^2]_m-X \qquad (M)$$

wherein:
n and m are independently 0, 1, 2, 3 or 4;
X is a halogen selected from F, Cl, Br, I;
$Ar^1$, $Ar^2$ are equal or different from each other and are aromatic moieties of the formula:

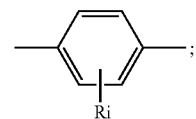

$Ar^3$ is selected from the group consisting of:

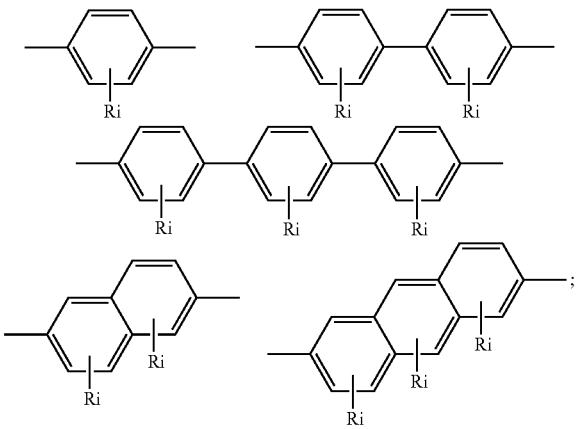

and each Ri is independently selected from the group consisting of: hydrogen, halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium; by reacting together at least one acid selected from the group consisting of sulfuric acid, arene sulfonic acid or oleum, at least one fluorinated anhydride; at least one halobenzene; at least one fluorinated acid a catalyst selected from the group consisting of boricacid, boronic acid, aluminosilicates, perfluoroalkanesulfonic acid resins, mixed oxides, and mixtures thereof; and, optionally, an aromatic compound; wherein the process is carried out in the absence of any solvent or in the presence of a solvent selected from the group consisting of: alkanes, chloroalkenes, chloroalkanes, halobenzenes and carbon disulfide, and the at least one fluorinated acid is added to the reaction.

17. The process according to claim 1, wherein the aluminosilicates are selected from the group consisting of acid-treated clays, zeolites, and mixtures thereof.

18. The process according to claim 17, wherein the aluminosilicates are montmorillonite K 10 and analogs, H-beta zeolite with a $SiO_2/al_2O_3$ ratio of $\leq 40$, and mixtures thereof.

19. The process according to claim 16, wherein the fluorinated acid is selected from the group consisting of perfluorinated alkane carboxylic acids, perfluorinated alkane sulfonic acids, and mixtures thereof.

20. The process according to claim 16, wherein the fluorinated acid is distilled off after the halobenzene is added to the reaction.

21. The process according to claim 16, wherein the molar ratio of the acid selected from the group sulfuric acid, arene sulfonic acid, or oleum to the halobenzene is from 0.2 to 5.

22. The process according to claim 21, wherein the molar ratio is from 0.4 to 2.

\* \* \* \* \*